(12) United States Patent
Takenaka et al.

(10) Patent No.: US 9,702,805 B2
(45) Date of Patent: Jul. 11, 2017

(54) AIRBORNE-SUBSTANCE DETECTION DEVICE AND CARTRIDGE USED IN SAME

(71) Applicant: Hitachi, Ltd., Tokyo (JP)

(72) Inventors: Kei Takenaka, Tokyo (JP); Shigenori Togashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 91 days.

(21) Appl. No.: 14/764,221

(22) PCT Filed: Jan. 29, 2013

(86) PCT No.: PCT/JP2013/051927
§ 371 (c)(1),
(2) Date: Jul. 29, 2015

(87) PCT Pub. No.: WO2014/118898
PCT Pub. Date: Aug. 7, 2014

(65) Prior Publication Data
US 2015/0377762 A1    Dec. 31, 2015

(51) Int. Cl.
*G01N 15/06* (2006.01)
*G01N 15/00* (2006.01)

(52) U.S. Cl.
CPC . *G01N 15/0612* (2013.01); *G01N 2015/0046* (2013.01)

(58) Field of Classification Search
CPC .................. G01N 15/0612; G01N 2015/0046
See application file for complete search history.

(56) References Cited

U.S. PATENT DOCUMENTS

2003/0136205 A1*   7/2003   Totoki ............... B01D 49/00
                                                      73/864.71

FOREIGN PATENT DOCUMENTS

| JP | 06160250 A | * | 6/1994 | ............. G01N 15/02 |
| JP | 2005-533502 A | | 11/2005 | |
| JP | 2006-345727 A | | 12/2006 | |
| WO | 2004/009840 A1 | | 1/2004 | |

OTHER PUBLICATIONS

International Search Report of PCT/JP2013/051927.

\* cited by examiner

*Primary Examiner* — Sally Merkling
(74) *Attorney, Agent, or Firm* — Mattingly & Malur, PC

(57) ABSTRACT

An airborne-substance detection device includes a cartridge and an optical detector. The cartridge includes: an inflow plate having formed therein a micropore that allows inflow of a microparticle-containing gas; a trapping plate disposed opposite the micropore and having the ability to capture the microparticles on a surface facing the micropore; and a main body in which the inflow plate and the trapping plate are installed, and in which a channel is formed that channels the gas to the micropore. The optical detector optically detects the microparticles captured on the trapping plate. The trapping plate is disposed on the outermost side of the cartridge, and is configured from a light transmissive member. The optical detector detects the captured microparticles on the trapping plate from the back side of the trapping plate.

5 Claims, 12 Drawing Sheets

AIRBORNE-SUBSTANCE DETECTION DEVICE AND CARTRIDGE USED IN SAME

TECHNICAL FIELD

The present invention relates to an airborne-substance detection device for detecting microparticles contained in breath or in air, and to a cartridge for use in such devices.

BACKGROUND ART

Various diagnoses and preventive techniques are used in the clinic to prevent spread of infections. For example, quick kits for easy and quick diagnosis of respiratory infections such as influenza are widely available. A diagnosis using a quick kit involves inserting a cotton swab into the nasal cavity of a patient to collect the bodily fluid from the nasal cavity, and detecting antigens of viruses, bacteria, and other microbes in the bodily fluid by immunochromatography.

Despite the simplicity of the diagnosis by the quick kit, it requires collecting antigens of microbes directly from the body of a patient. The procedure thus qualifies as medical practice, and limited to only healthcare professionals. This has created a need for a method that can be used to more conveniently detect microbes. To this end, there has been proposed a method that directly traps viruses, bacteria, and other air-borne microbes from the breath, and detects these microbes by way of gene amplification and image processing.

Patent Literature 1 describes an example of microbe detection from breath. In the microbe detection system of this publication, microbes in air are trapped by impaction at the surface of the trapping section of a microbe detection chip, and the trapped microbes are eluted into a liquid. The liquid containing the microbes is then transferred to a different chip to detect the microbes through gene amplification.

Another example of microbe detection is described in Patent Literature 2. This publication uses a system that uses a membrane method to capture and detect microbes. Specifically, a pored membrane is disposed between a top surface part and a bottom surface part, and used to capture microbes larger than the pores and contained in a fluid. The captured microbes are stained with a visualization reagent for observation and analysis by image processing with a CCD camera, or by inspection with an electron microscope or the like.

CITATION LIST

Patent Literature

Patent Literature 1: JP-A-2006-345727
Patent Literature 2: JP-T-2005-533502

SUMMARY OF INVENTION

Technical Problem

Quick kits are effective as an easy and quick method of infection diagnosis. However, a quick kit requires inserting a cotton swab inside the nasal cavity of a patient to collect the bodily fluid, and this can be painful and may cause rejection from little patients. Another typical drawback of quick kits is the poor sensitivity, and the microbe antigens may not be obtained in sufficient amounts from patients in early stages of infection. Such small antigen amounts from the collected microbes may yield a negative result. Quick kits are thus not necessarily effective in terms of preventing infections. The act of inserting a cotton swab into the nasal cavity of a patient is medical practice, and is limited to only healthcare professionals.

On the other hand, the method that directly traps airborne microbes by impaction or filtration as described in Patent Literature 1 or 2 enables collecting microbes without causing pain in a patient, and, since it does not qualify as medical practice, can be practiced by non-healthcare professionals. However, the method described in Patent Literature 1 uses different chips for the trapping and the detection, and requires changing the microbe-containing liquid. Further, because the detection is based on gene amplification, the method takes several hours to purify and amplify microbe genes, making it difficult to quickly obtain test results.

The microbe detection method described in Patent Literature 2 directly detects the microbes trapped on a membrane, and enables trapping and detection both automatically and continuously. The method also enables accurate measurements by distinguishing microbes from microparticles such as dust with information such as the size and shape of the subject, staining by a visualization reagent, and light intensity.

However, the method described in Patent Literature 2 obtains an image by irradiation of a filter surface with excitation light via the upper part and a cavity, and may produce an unclear image under the influence of the refraction at the boundary between the upper part and the cavity, and the reflection or scattering of light at the filter surface. The method also requires taking a high-magnification image to distinguish the shapes of microbes measuring several micrometers in size. However, it is very time consuming to obtain an image for the whole surface of the membrane of several millimeter square, and distinguish microbes from the obtained image. This makes it difficult to quickly obtain test results.

The invention has been made in view of the problems of the related art, and it is an object of the invention to enable convenient and accurate detection of microbes from breath or air with an airborne-substance detection device detachably provided with a gas sealed container such as a breath bag, and a cartridge. Another object of the invention is to enable easy and accurate microparticle detection with a disposable cartridge for use in the airborne-substance detection device.

Solution to Problem

One feature of the invention directed to achieving the foregoing objects is a cartridge for airborne-substance detection devices that includes:

an inflow plate having formed therein a micropore that allows inflow of a microparticle-containing gas;

a trapping plate disposed opposite the micropore and having the ability to capture the microparticles on a surface facing the micropore; and a main body in which the inflow plate and the trapping plate are installed, and in which a channel is formed that channels the microparticle-containing gas to the micropore, wherein the trapping plate is disposed on the outermost side of the cartridge with the trapping surface facing inward, and is configured from a light transmissive member.

Another feature of the invention is an airborne-substance detection device that includes the cartridge for airborne-substance detection devices, and an optical detector for optically detecting the microparticles captured on the trapping plate, wherein the trapping plate is disposed on the outermost side of the cartridge, and is configured from a light transmissive member, and wherein the optical detector is disposed on the back side of the trapping surface of the trapping plate.

Advantageous Effects of Invention

In the invention, optical detection of microparticles is performed from the back side of the cartridge trapping plate in an airborne-substance detection device detachably provided with a sealed container such as a breath bag, and a cartridge. The airborne-substance detection device can thus conveniently and accurately detect the microbes contained in breath. Detection from the back side of the trapping plate of the cartridge is made possible by the translucency of the trapping plate.

DESCRIPTION OF EMBODIMENTS

Some embodiments of the invention are described below with reference to the accompanying drawings. As used herein, the detection target microbe contained in air or breath has wider meaning than the common definition of microbe, and encompasses viruses, bacteria, yeasts, protozoa, fungi, spores, and pollen.

Figure 1:
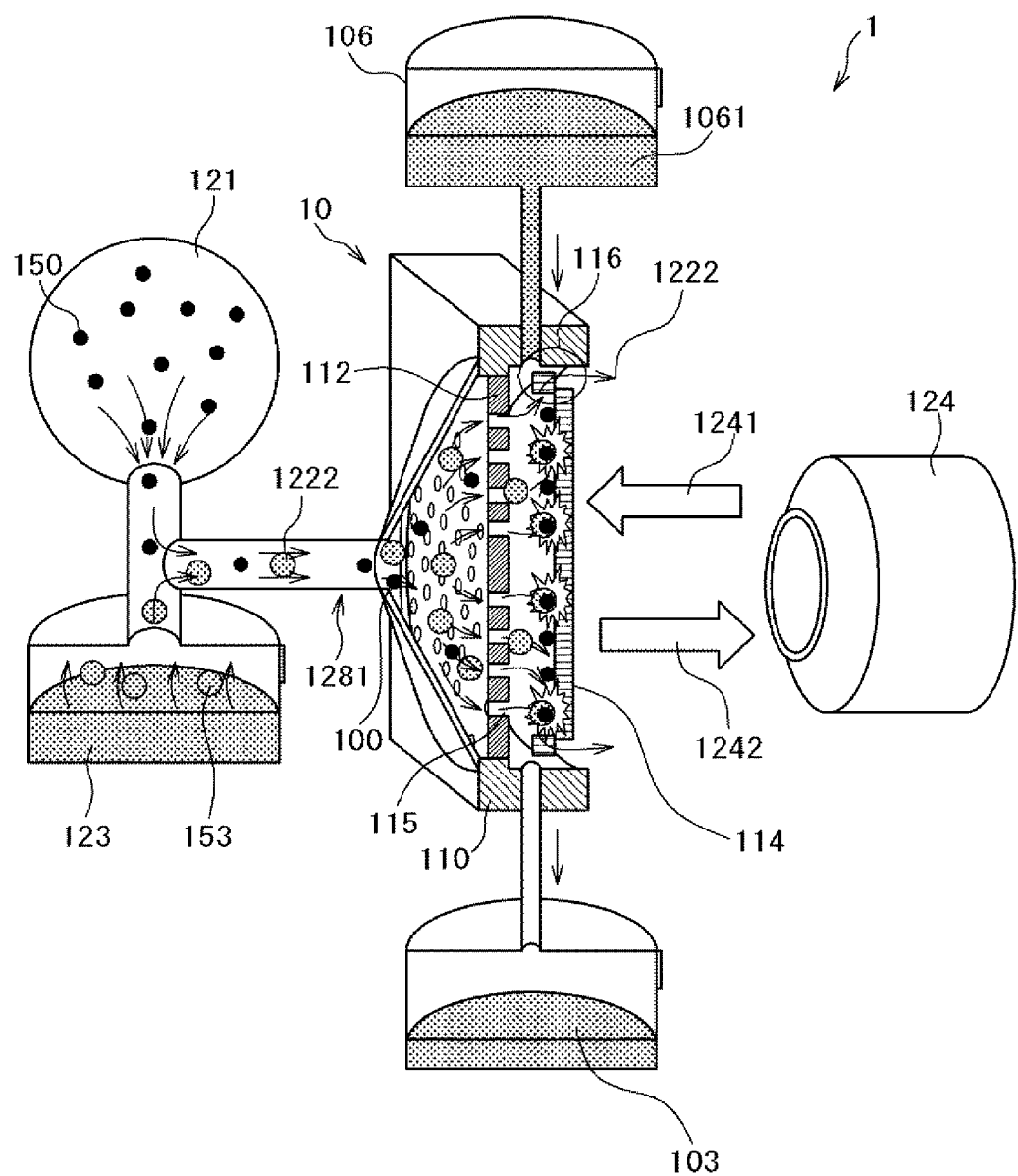
FIG. 1 is a schematic view representing the principle of a breath microbe detection device according to the invention.

FIG. 1 schematically represents a breath microbe detection device 1 as one form of the airborne-substance detection device according to the invention. The figure shows a partial cross section of the breath microbe detection device 1. The breath microbe detection device 1 has a cartridge 10 detachably installed on one side surface of the box-shaped detection device main body. A breath bag 121 sealing the patient breath collected at the site of the breath microbe detection device 1 or in a remote location is connected to the cartridge 10 via a connecting tube 1281.

The cartridge 10 has a form of a flat rectangular box or a thick card. Inside a rectangular main body 110 are a porous plate (inflow plate) 112 with a plurality of micropores 115, and a trapping plate 114 disposed substantially parallel to the porous plate 112 with a small distance therefrom. An inlet 100 is formed at the central portion on a flat side surface of the main body 110 to attach and detach the connecting tube 1281 used to connect the breath bag 121.

The breath microbe detection device 1 has a pump (not shown) for drawing the breath out of the breath bag 121. The pump draws the breath out of the breath bag 121 toward the cartridge 10, as indicated by arrows 1222. The breath introduced through the inlet 100 of the main body 110 from the breath bag 121 passes through the micropores 115 of the porous plate 112, and collides with the surface of the light transmissive trapping plate 114 in the form of a jet flow. The jet flow of breath changes its course at the surface portion of the trapping plate 114, upon which microbe particles 150 contained in the breath deviate from the air flow under the inertial force, and are trapped on the surface of the trapping plate 114 upon colliding the surface. The breath having passed through the micropores 115 and from which the microbe particles 150 have been removed discharges from the cartridge 10 through vent holes 116, gaps formed between the end surfaces of the trapping plate 114 and the inner surfaces of the main body 110. This method is called impaction.

An optical detector 124 for optically detecting the microbe particles 150 trapped on the trapping plate 114 is disposed on the back side of the trapping plate 114, inside the main body of the breath microbe detection device 1. The optical detector 124 shines excitation light 1241 on the microbe particles 150 trapped on the surface of the trapping plate 114. Upon irradiation of light, the optical detector 124 detects the generated fluorescence 1242 from the microbe particles 150 to detect the presence of microbe particles 150 in the breath. Here, the light transmissive trapping plate 114 is the only member that is disposed between the optical detector 124 and the microbe particles 150, and the influence of light refraction, reflection, and scattering can be eliminated as much as possible. This enables detecting of even weak fluorescence of the microbe particles 150.

The breath microbe detection device 1 labels the trapped microbe particles 150 with a specific fluorescent dye so that the microbe particles 150 can fluoresce. For the detection of specific microbes such as influenza virus and tuberculosis, fluorescent dyes that specifically bind to these specific microbes are used to improve detection sensitivity and discrimination performance. For example, a fluorescence-labeled anti-influenza virus antibody is used for influenza virus, and a fluorescence-labeled anti-tuberculosis antibody is used for tubercle bacilli.

An atomizer 123 for atomizing liquid is connected to the middle of the connecting tube 1281 connecting the breath bag 121 to the main body 110 of the cartridge 10. The atomizer 123 stores a fluorescent dye solution, and atomizes the fluorescent dye solution contained therein to generate a fluorescent dye-containing mist 153.

With the microbe particles 150 trapped on the trapping plate 114, the mist 153 generated by the atomizer 123 is jetted onto the surface of the trapping plate 114 through the micropores 115. The fluorescent dye contained in the mist 153 jetted through the micropores 115 and collided with the trapping plate 114 specifically binds to the microbe particles 150 trapped on the surface of the trapping plate 114, and labels the microbe particles 150. Upon labeling the microbe particles 150, the fluorescent dye specifically binding to the microbe particles 150 is excited by the excitation light 1241 from the optical detector 124, and generates fluorescence 1242. The generated fluorescence 1242 is detected by the optical detector 124.

The breath microbe detection device 1 is provided with a reagent container 106 for storing a reagent 1061, and a waste liquid container 103 for retaining the reagent 1061 after it is used. The reagent container 106 and the waste liquid container 103 are provided as an integral unit with the cartridge 10, or separately from the cartridge 10. The reagent 1061 is, for example, a washing liquid, or a fluorescent dye solution. In the case of a washing liquid, the reagent 1061 takes no part in labeling of the microbe particles 150, and is used to remove the fluorescent dye remaining in the vicinity of the trapping plate 114, or to facilitate a smooth transition to the next detection procedure by the cartridge 10 after finishing detection with the optical detector 124. In the case of a fluorescent solution, the reagent 1061 is used for the labeling of the microbe particles 150 with the fluorescent dye.

The pump (not shown) is operated to supply the reagent 1061 from the reagent container 106 to the surface of the trapping plate 114. The reagent 1061 is then discharged into the waste liquid container 103 after it is used to wash the surface of the trapping plate 114 or label the microbe particles.

In the microbe detection by the breath microbe detection device 1 according to the invention, a tester only needs to connect the breath bag 121 with the patient breath to the breath microbe detection device 1, and the rest of the process is automatic. Specifically, connecting the breath bag 121 activates the pump, and the microbe particles 150 in the breath are automatically trapped on the surface of the trapping plate 114 in the cartridge 10. The fluorescent dye from the atomizer 123 or the reagent container 106 is sent to the trapped microbe particles 150, and specifically binds to the microbe particles 150. The optical detector 124 automatically detects the fluorescence from the fluorescent dye forming specific bonds, and detects the microbe particles 150.

In FIG. 1, the reagent container 106 and the waste liquid container 103 for the reagent 1061 are separately provided from the cartridge 10, and the fluorescent dye solution is stored in the atomizer 153 that generates the mist 153. However, the fluorescent dye may be stored in the reagent container 106, and the reagent container 106 and the waste liquid container 103 may be formed inside the cartridge 10, as will be described later.

The cartridge 10 is described in more detail with reference to FIG. 2A to FIG. 4.

Figure 2A:
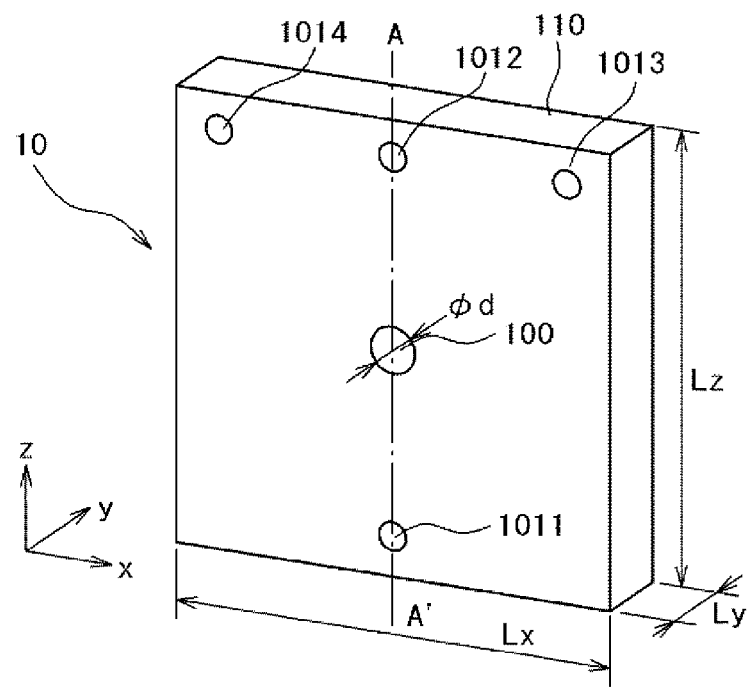
FIG. 2A is a front perspective view of an example of the cartridge according to the invention.
Figure 2B:
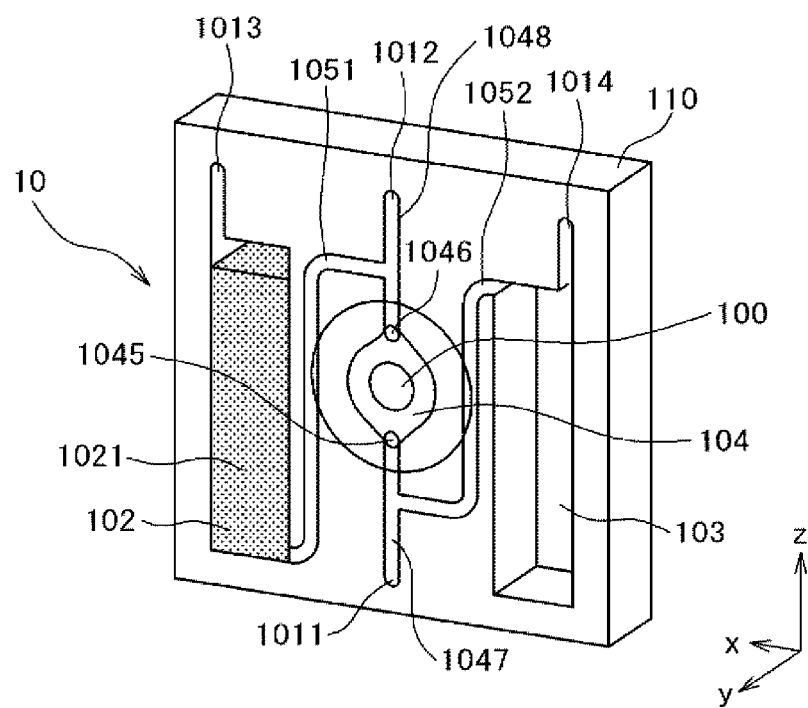
FIG. 2B is a back perspective view of the cartridge shown in FIG. 2A.
Figure 3A:
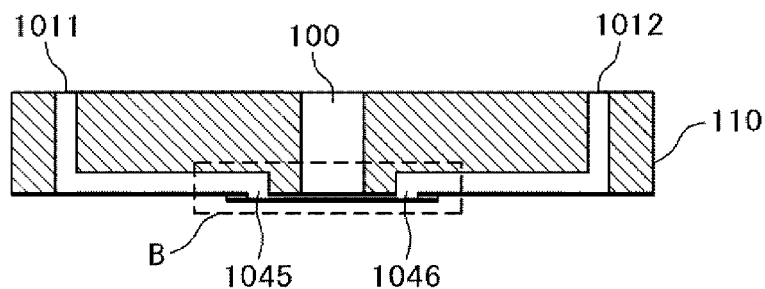
FIG. 3A is a cross sectional view at line A-A' of FIG. 2A.
Figure 3B:
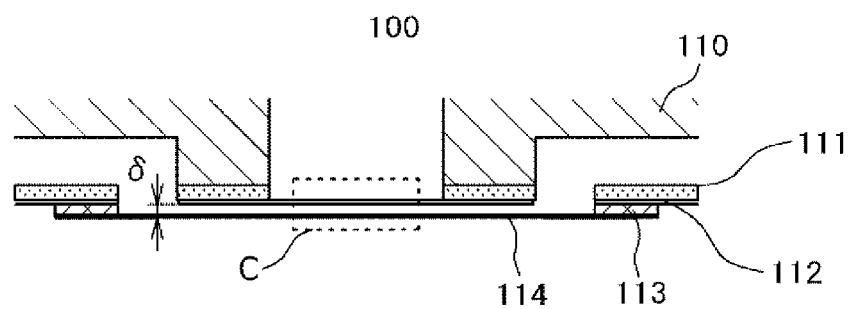
FIG. 3B is an enlarged view of portion B of FIG. 3A.
Figure 3C:
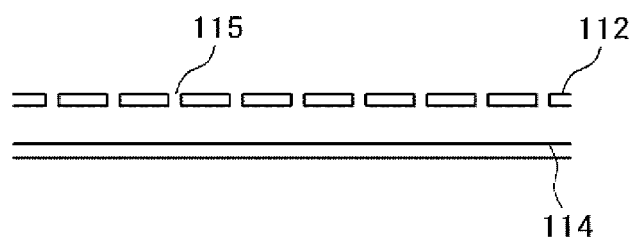
FIG. 3C is an enlarged view of portion C of FIG. 3B.

FIG. 2A is a front perspective view of the cartridge 10, and FIG. 2B is a perspective view on the back side of the cartridge 10. FIG. 3A is a cross sectional view at line A-A' of FIG. 2A, FIG. 3B is an enlarged view of portion B of FIG. 3A, and FIG. 3C is an enlarged view of portion C of FIG. 3B.

The cartridge 10 has a mechanism to maintain liquid inside the cartridge 10, and to perform the steps necessary for trapping and detecting the microbes present in breath or air. The inlet 100 where the connecting tube 1281 in communication with the breath bag 121 is detachably connected is formed in the central portion on the front side of the main body 110 occupying the majority of the cartridge 10. The breath or air containing microbes flows into the inlet 100 from the breath bag 121. At the periphery of the cartridge 10 is a plurality of vent holes 1011 to 1014, which are used to vary the pressure inside a plurality of channels 1051 and 1052 (will described later in detail) formed inside the cartridge 10, and control the flow of fluids such as the breath, the reagent, and the washing liquid.

A trapping detector 104 for trapping and detecting microbe particles is provided at the central portion on the back side of the main body 110, corresponding in position to the inlet 100, as shown in FIG. 2B. A washing liquid container 102 storing a washing liquid 1021 for washing the trapping detector 104 is formed on one side of the main body 110 (left side in FIG. 2B). A waste liquid container 103 for storing the washing liquid 1021 having passed through the trapping detector 104 is formed on the other side (right side in FIG. 2B) of the main body 110, opposite the washing liquid container 102 with respect to the trapping detector 104.

The washing liquid container 102 and the trapping detector 104 are connected to each other with a communication channel 1051 formed in the main body 110 for the washing liquid container 102 and the trapping detector 104. The waste liquid container 103 and the trapping detector 104 are connected to each other with a communication channel 1052 formed in the main body 110 for the waste liquid container 103 and the trapping detector 104. The terms "upstream" and "downstream" used in the descriptions below are relative to the washing liquid container 102 and the waste liquid container 103 with respect to the direction of flow of the washing liquid 1021.

The vent hole 1012 provided at the upper center of the main body 110 is in communication with the communication channel 1051 that connects the washing liquid container 102 and the trapping detector 104 to each other. In the same fashion, the vent hole 1013 is in communication with the upper part of the washing liquid container 102, and the vent hole 1014 is in communication with the upper part of the waste liquid container 103. The vent hole 1011 is provided at the lower center of the main body 110, and is in communication with the communication channel 1052 that connects the waste liquid container 102 and the trapping detector 104 to each other.

The terminal of the communication channel 1051 of the washing liquid container 102 and the trapping detector 104 forms a branched channel 1048 with two branches, one of the branches ending at the vent hole 1012, and the other extending to the trapping detector 104 and forming a junction 1046 to the trapping detector 104. Similarly, the terminal of the communication channel 1052 of the waste liquid container 103 and the trapping detector 104 forms a branched channel 1047 with two branches, one of the branches ending at the vent hole 1011, and the other extending to the trapping detector 104 and forming a junction 1045 to the trapping detector 104.

Figure 4:
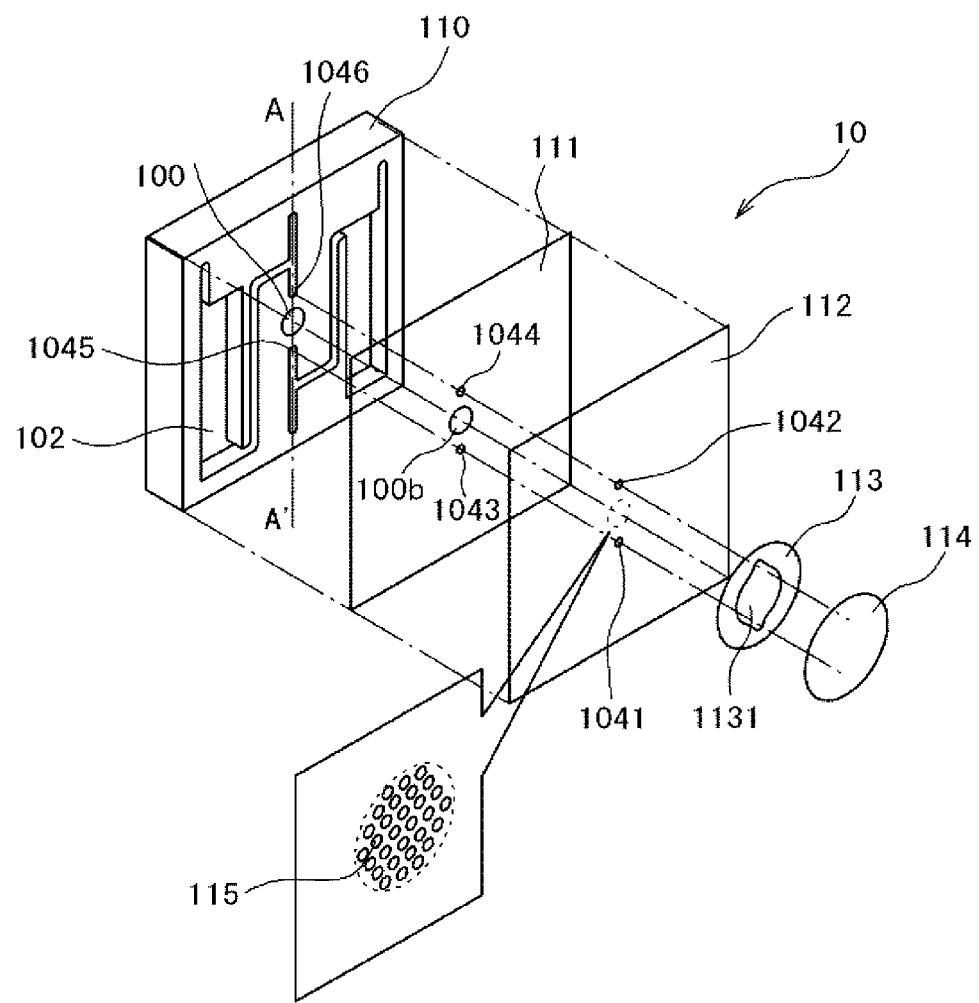
FIG. 4 is an exploded perspective view of the cartridge shown in FIG. 2A.

FIG. 4 shows an exploded perspective view of the cartridge 10. As described above, the main body 110 has the containers 102 and 103, the channels 1047, 1048, 1051, and 1052, and the vent holes 1011 to 1014, and 1045 and 1046. For easy fabrication of the containers 102 and 103, the channels 1047, 1048, 1051, and 1052, and other such components, the main body 110 uses a waterfast resin material, taking into consideration processibility and manufacturing cost. Examples of such waterfast resin materials include polypropylene, polyethylene terephthalate, polycarbonate, polystyrene, acrylonitrile butadiene styrene resins, and polymethylmethacrylate ester. The containers 102 and 103, and the channels 1047, 1048, 1051, 1052 are formed in the main body 110 by the injection molding of these materials.

A sheet-like adhesive layer 111 with adhesive-coated surfaces is bonded to the back side of the porous plate 112 to bond the porous plate 112 to the main body 110. This seals the containers 102 and 103, and the channels 1047, 1048, 1051, and 1052. At a central portion of the adhesive layer 111 are a communication hole 100b corresponding in position to the inlet 100, and communication holes 1043 and 1044 corresponding in position to junctions 1045 and 1046, respectively.

The adhesive layer 111 is a component provided to bond the main body 110 and the porous plate 112 to each other, and as such an acrylic- or silicone-based adhesive agent may be used instead of the adhesive-coated sheet. The adhesive layer 111 is not needed when the main body 110 and the porous plate 112 are bonded by using a method such as ultrasonic bonding.

The porous plate 112 with the micropores 115 formed at the central portion of the plate is bonded to the back side of the adhesive layer 111. Communication holes 1041 and 1042 are formed more toward the periphery of the porous plate 112 than the micropores 115, corresponding in position to the communication holes 1043 and 1044 of the adhesive layer 111.

Light transmissive resin materials, such as polyethylene terephthalate, polymethylmethacrylate ester, and cycloolefin polymers, that do not easily generate stray light or autofluorescence are used for the porous plate 112 to avoid noise in the fluorescence detection of the microbe particles 150 labeled with a fluorescent dye 154. The micropores 115 are formed in the porous plate 112 by using a microfabrication technique such as machining, ultrasonic machining, etching, and laser machining.

For the impaction trapping of microbe particles 150, the micropores 115 are formed in smaller diameters to trap microbe particles 150 of smaller particle sizes. The micropores 115 need to be formed in larger numbers as the draw rate of microbe particles 150 is increased. The optimum diameter and the optimum number of micropores 115 thus depend on the measurement target.

For example, in a test intended to detect particles of sizes ranging from viral particles with a diameter of 0.3 μm to pollen with a diameter of several ten micrometers at a draw rate of 0.001 m³/min to 1 m³/min, about 1 to 10,000 micropores 115 having a diameter of 0.01 m to 3 mm are provided at 0.05 mm to 15 mm intervals. As a typical example, 100 micropores 115 having a diameter of 0.1 mm are provided at the interval of 0.6 mm when breath air containing viral particles of 0.3 jam and greater diameters is drawn at a draw rate of 0.003 m³/min.

A ring-like spacer 113 with an opening 1131 formed at the central portion of the ring is bonded to the back side of the porous plate 112 in a portion around the micropores 115. The spacer 113 has a form of a sheet with adhesive-coated surfaces, and the trapping plate 114, having about the same outer diameter as the spacer 113, is bonded to the adhesive surface of the spacer 113. By being interposed between the porous plate 112 and the trapping plate 114, the spacer 113 forms a predetermined gap δ between these two plates 112 and 114 (see FIG. 3B).

The spacer 113 is made of waterfast resin material, and may use resins such as polypropylene, polyethylene terephthalate, polycarbonate, polystyrene, acrylonitrile butadiene styrene resin, and polymethylmethacrylate ester. For the impaction trapping of microbe particles, the thickness of the spacer 113 is about 1 to 10 times the diameter of the micropores 115. For example, the spacer 113 has a thickness of 0.1 mm to 1 mm when the diameter of the micropores 115 is 0.1 mm.

The trapping plate 114 serves not only as the receptacle for trapping the microbe particles 150, but as a photoconducting path of the excitation light 1241 and the fluorescence 1242 in the fluorescence detection by the optical detector 124. For this reason, the trapping plate 114 uses a material having a light transmittance of 80% or more and weak autofluorescence in a near ultraviolet to near-infrared wavelength region, specifically a wavelength region of 300 nm to 800 nm. The material of the trapping plate 114 may be glass or quartz, or a light transmissive resin such as polyethylene terephthalate, polymethylmethacrylate ester, cycloolefin polymer, and polydimethylsiloxane. Alternatively, different members configured from these materials may be bonded to each other as the material of the trapping plate 114. The trapping plate 114 has a thickness of about 0.1 mm to 10 mm.

An adhesive substance may be coated or attached to the surface of the trapping plate 114 to ensure trapping of the collided microbe particles 150. Alternatively, the surface of the trapping plate 114 may be decorated by physical or chemical bonding with antibodies, artificial antibodies, and other such substances that specifically bind to specific microbe particles.

The lengths Lx and Lz along the width and height directions (x and z directions, respectively) of the cartridge 10 configured as above are about 10 mm to 300 mm, and the length Ly along the thickness direction (y direction) is about 3 mm to 100 mm. The diameter φd of the inlet 100 is about 1 mm to 100 mm. The washing liquid container 102 is sized to have a volume Lw large enough to store about 0.1 ml to 100 ml of washing liquid 1021. The channel 1051 connecting the washing liquid container 102 and the trapping detector 104, and the channel 1014 connecting the trapping detector 104 and the waste liquid container 103 have a depth and a width of about 0.1 mm to 10 mm. Typically, Lx and Lz are about 60 mm, and Ly is about 10 mm.

Figure 5:
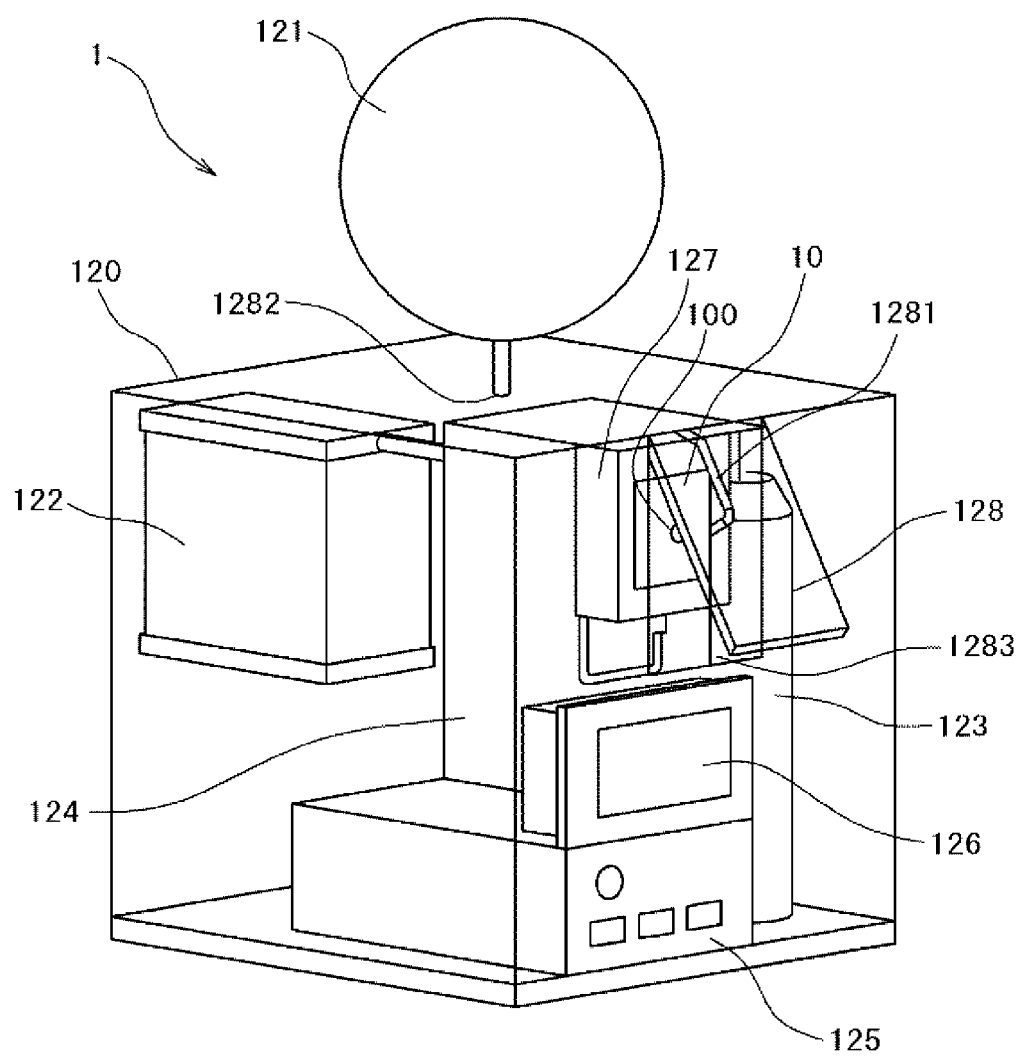
FIG. 5 is a perspective view of a breath microbe detection device with the cartridge shown in FIG. 2A.

FIG. 5 is a perspective view of the breath microbe detection device 1 housing the cartridge 10. In the breath microbe detection device 1, an attachment opening 1282 for the breath bag 121 is formed on the top surface so that the breath bag 121 with the patient's breath can be freely attached and detached. The attachment opening 1282 is connected to a connecting tube 1281 that is routed inside the breath microbe detection device 1. The end of the connecting tube 1281 is interdigitatable with the inlet 100 formed at the central portion of the cartridge 10.

The cartridge 10 that traps and detects the breath microbes is housed in the cartridge holder 127 provided in the vicinity of a window portion 1283 formed in the upper part on one side surface of the breath microbe detection device 1. The breath microbe detection device 1 is sealed after the cartridge 10 is housed inside the cartridge holder 127, and the window portion 1283 has a lid 128 that can be opened and closed. The lid 128 is fixed to the connecting tube 1281. This allows the end of the L-shaped connecting tube 1281 to automatically interdigitate with the inlet 100 of the cartridge 10 upon closing the window portion 1283 with the lid 128.

The optical detector 124 provided for the fluorescence detection of the microbe particles trapped in the cartridge 10 is disposed on the back side of the breath microbe detection device 1. On the back side of the optical detector 124 is disposed a pump 122 that creates a reduced pressure in the channels (e.g., channels 1051, 1052) formed in the cartridge 10, and draws the breath inside the breath bag 121 or the mist of the fluorescent dye atomized by the atomizer 128 into the cartridge 10.

The atomizer 123 that atomizes the liquid containing the fluorescent dye that specifically binds to the microbes in the breath is disposed on the side portion of the cartridge holder 127 inside the breath microbe detection device 1. Beneath the cartridge holder 127 are a control section 125 for controlling the operation of the breath microbe detection device 1, and a display section 126 for displaying the test contents and the test results. FIG. 5 is shown as having the control section 125 and the display section 126 incorporated inside the breath microbe detection device 1. However, externally connected devices such as a personal computer may be used instead.

Figure 6:
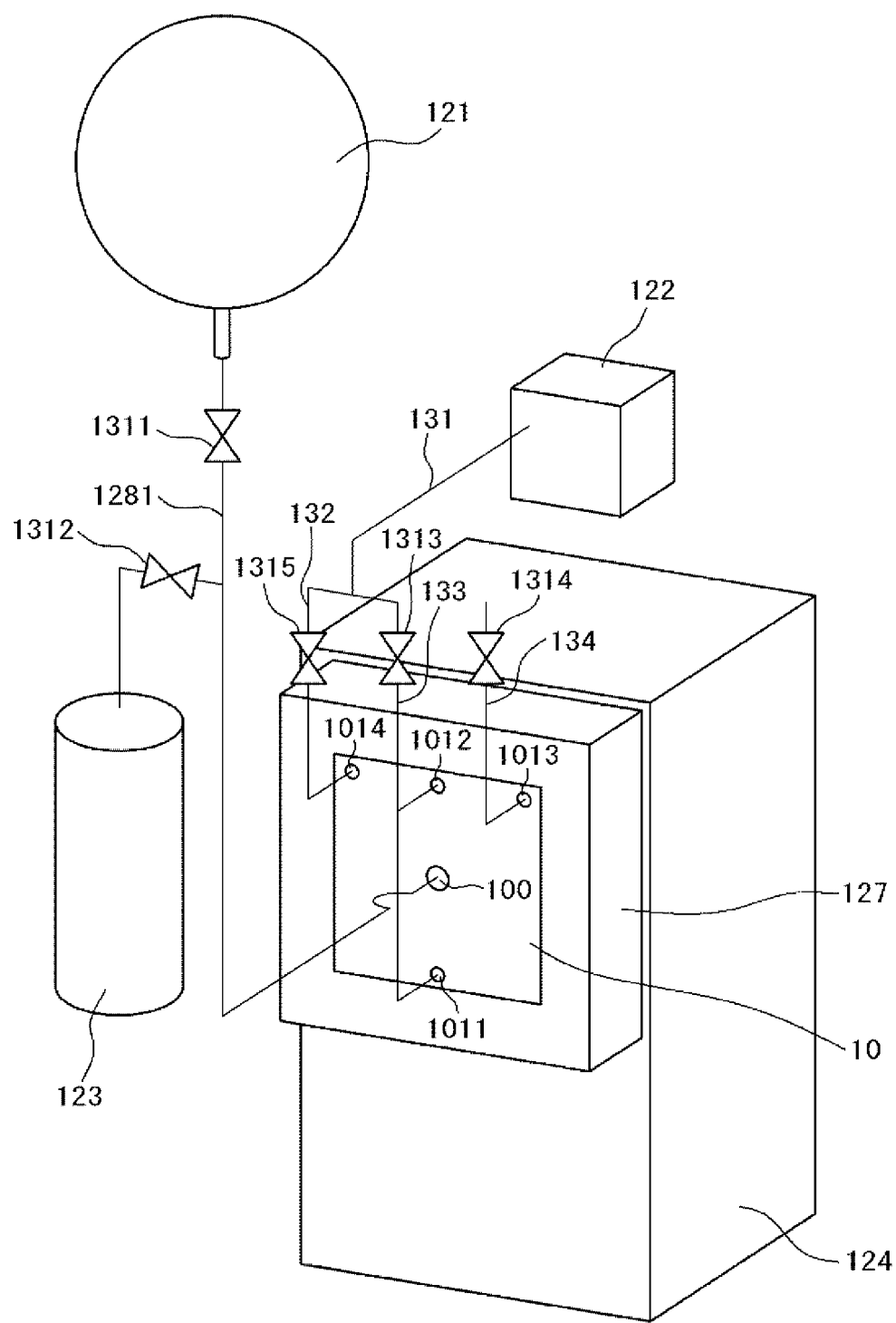
FIG. 6 is a piping system diagram of the breath microbe detection device shown in FIG. 5.

FIG. 6 is a diagram showing the piping system of the channels from the breath bag 121 and the atomizer 123 to the cartridge 10. The breath bag 121 has a valve (not shown) that prevents leaking of the collected breath. The valve automatically opens upon attaching the breath bag 121 to the breath microbe detection device 1.

The breath microbe detection device 1 has a valve 1311 on the connecting tube 1281 of the breath bag 121, and a valve 1312 in the middle of the pipe branching out from the connecting tube 1281 into the atomizer 123. The end of the connecting tube 1281 is connected to the inlet 100 of the cartridge 10, as described above.

The intake pipe 131 of the pump 122 branches into a plurality of piping systems. One of the piping systems, 132, is connected to the vent hole 1014 that is in communication with the waste liquid container 103 of the cartridge 10, and the other piping system 133 is connected to the vent hole 1012 that is in communication with the washing liquid container 102, and to the vent hole 1011 that is in communication with the waste liquid container 103. Valves 1315 and 1313 are interposed in the pipes 132 and 133, respectively. A pipe 134 that is open to the atmosphere is connected to the vent hole 1013 that is in communication with the washing liquid container 102 of the cartridge 10. A valve 1314 is attached to the pipe 134. The valves are provided inside the breath microbe detection device 1.

Example 1

Figure 7:
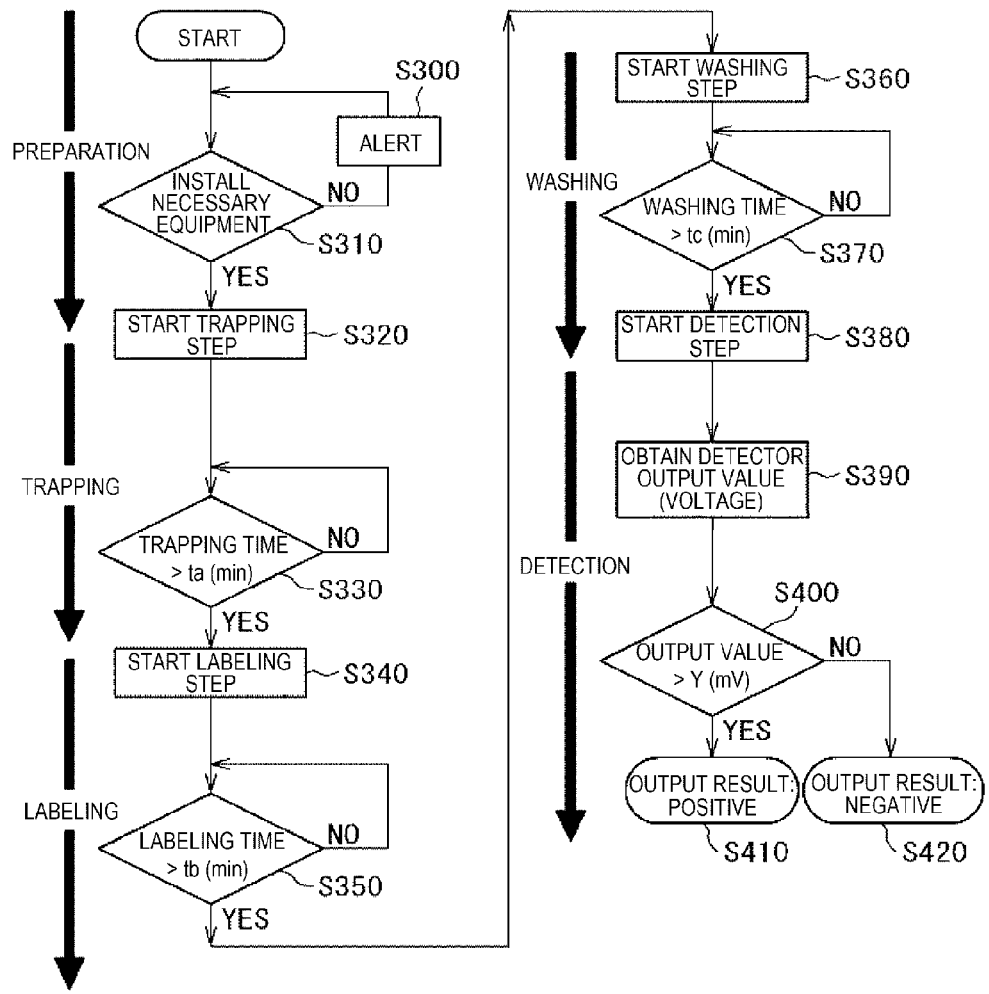
FIG. 7 is a flowchart of microbe detection by the breath microbe detection device.
Figure 8A:
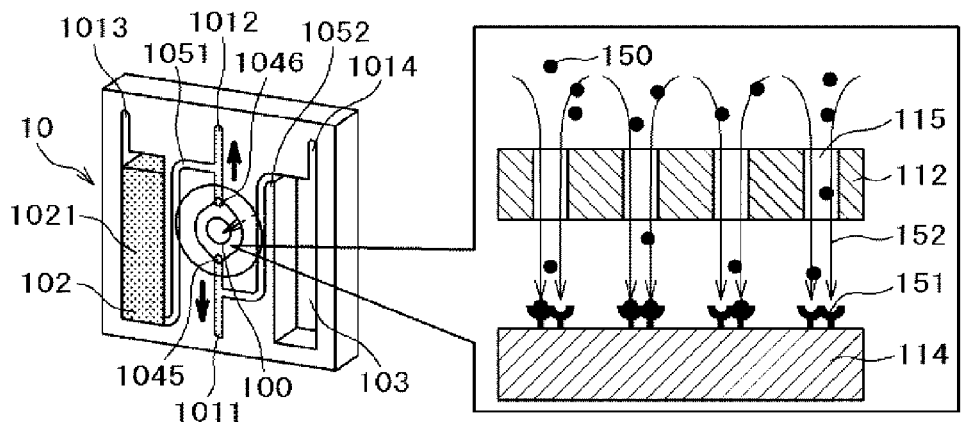
FIG. 8A is a diagram representing the operation of the cartridge shown in FIG. 2A, explaining the microbe trapping step.
Figure 8B:
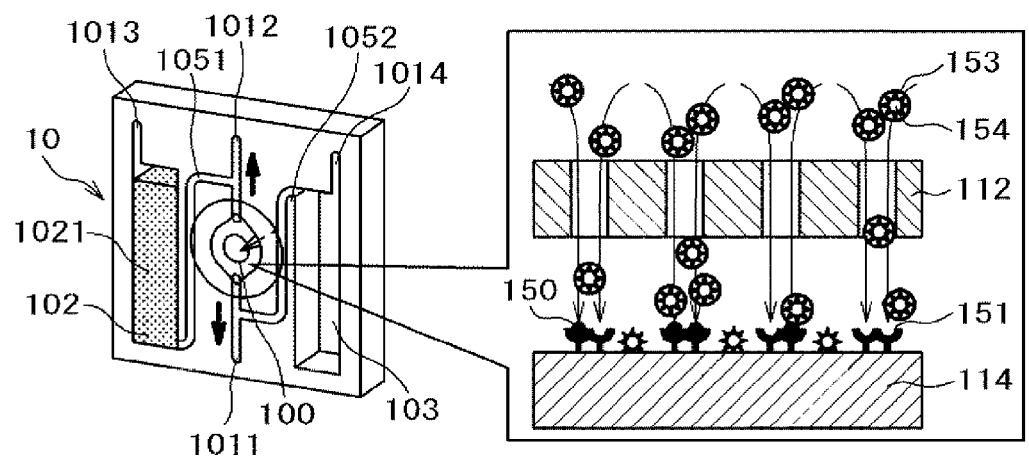
FIG. 8B is a diagram representing the operation of the cartridge shown in FIG. 2A, explaining the microbe labeling step.
Figure 8C:
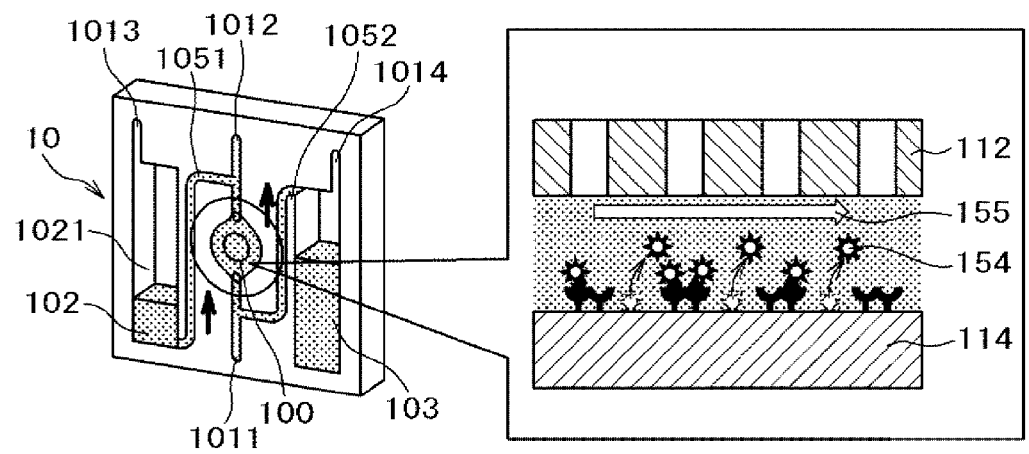
FIG. 8C is a diagram representing the operation of the cartridge shown in FIG. 2A, explaining the microbe washing step.
Figure 9:
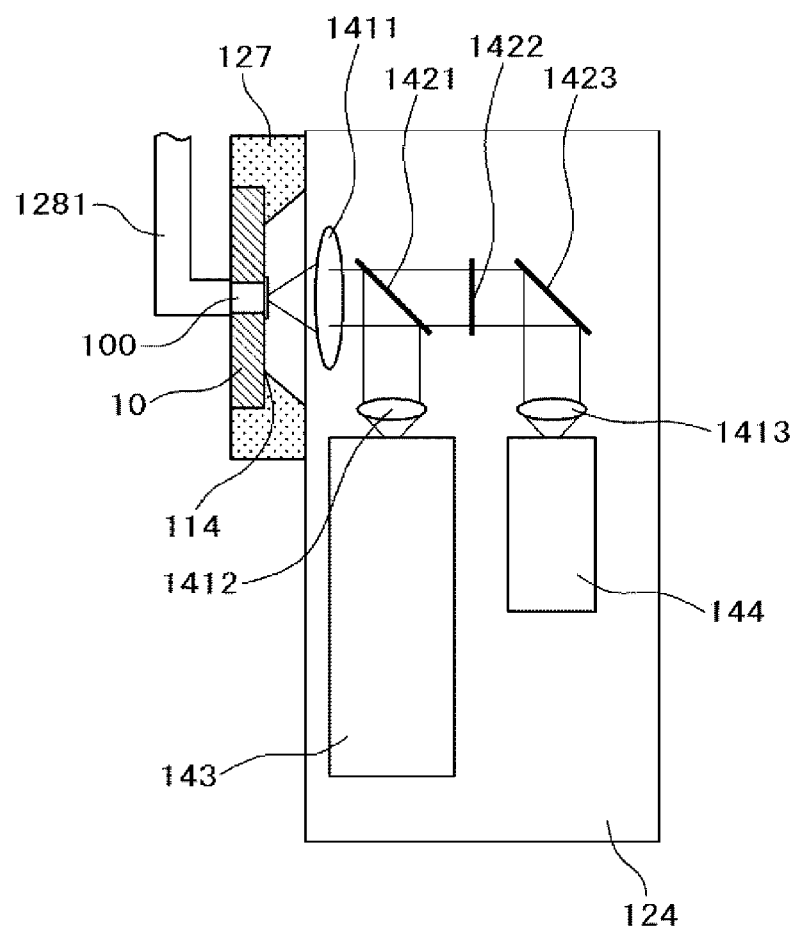
FIG. 9 is a schematic view of an optical detector provided in the breath microbe detection device shown in FIG. 5.
Figure 10:
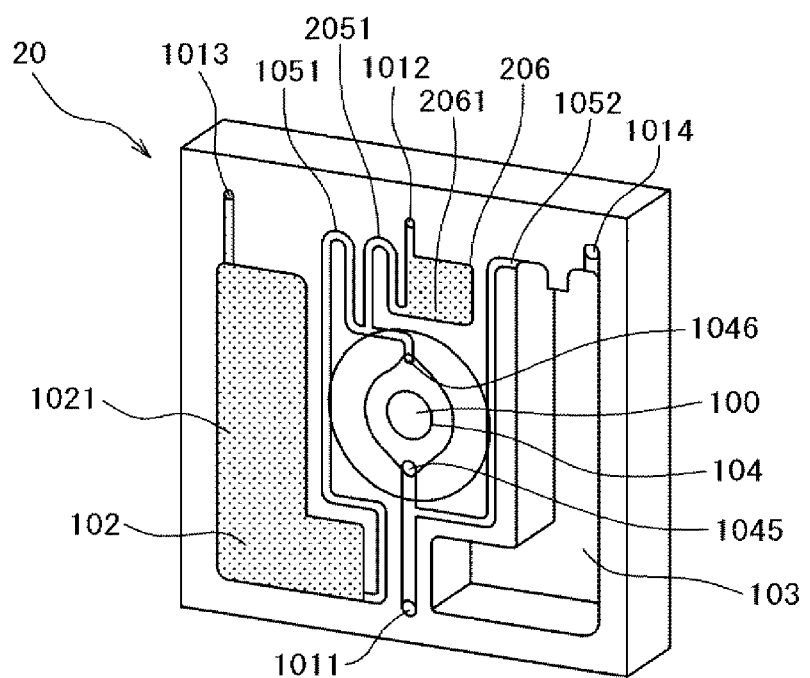
FIG. 10 is a perspective view of another example of the cartridge according to the invention.

The following describes the operation of the breath microbe detection device 1 in steps, and the open/close state of the valves 1311 to 1315 in each step, with reference to FIG. 7 to FIG. 8C. FIG. 7 is a flowchart of breath microbe particle detection by the breath microbe detection device 1, representing the preparation, trapping, labeling, washing, and detection steps. FIGS. 8A to 8C are diagrams representing the flow state inside the cartridge 10 in the trapping, labeling, and washing steps, and the flow state of the microbe particles 150 and the fluorescent dye 154 against the trapping plate 114.

(0) Preparation Step

In order to start the breath microbe detection procedure, a tester installs the breath bag 121 with the patient's breath, and the cartridge 10 in the breath microbe detection device 1, and closes the lid 128. For testing, the tester then designates test contents through input means provided in the control section 125. This information is displayed on the display section 126. The control section 125 in step S310 checks whether the necessary equipment, including the cartridge 10 and the breath bag 121, are installed in the breath microbe detection device 1. The display section 126 displays an alert if the necessary equipment is not installed or attached (step S300). The trapping step starts upon completion of the preparation (step S320).

In this Example, the test subject is the patient's breath. However, for example, a bag sealing the surrounding air of interest may be used instead of the breath bag 121 to detect subjects contained in the surrounding air, for example, such as microbe particles, allergens (e.g., fragmented animal skin, feces and dead bodies of mites, and house dust), gas emission particles, and ore particles (e.g., asbestos).

Table 1 shows the states of the valves 1311 to 1315, the pump 122, and the optical detector 124 in each step. The trapping, labeling, washing, and detection steps are described below with reference to Table 1, FIG. 7, and FIGS. 8A to 8C.

TABLE 1

| Step | Valve | | | | | Pump | Detector |
| | 1311 | 1312 | 1313 | 1314 | 1315 | 122 | 124 |
|---|---|---|---|---|---|---|---|
| Trapping | Open | Closed | Open | Closed | Closed | On | Off |
| Labeling | Closed | Open | Open | Closed | Closed | On | Off |
| Washing | Closed | Closed | Closed | Open | Open | On | Off |
| Detection | Open | Open | Open | Open | Open | Off | On |

(1) Trapping Step

In the trapping step, the valve 1311 provided for the connecting tube 1281 connecting the breath bag 121 and the inlet 100 of the cartridge 10 is opened. Another valve that is opened in this step is the valve 1313 provided for the pipe 133 connecting the pump 122 to the vent hole 1011 that is in communication with the upstream side of the waste liquid container 103 of the cartridge 10, and to the vent hole 1012 that is in communication with the downstream side of the washing liquid container 102. Operating the pump 122 thus draws the breath out of the breath bag 121 into the inlet 100 and the vent holes 1011 and 1012 of the cartridge 10, as shown in FIG. 8A.

The valve 1314 provided for the pipe 134 connected to the vent hole 1013 formed at the upper end portion of the washing liquid container 1013, and the valve 1315 provided for the pipe 132 connected to the vent hole 1014 formed at the upper end portion of the waste liquid container 103 are closed. With these valves closed, the washing liquid 1021 inside the washing liquid container 102 of the cartridge 10 remains in the washing liquid container 102.

In this state, the microbe particles 150 contained in the breath pass through the micropores 115 of the porous plate 112, and collide with the trapping plate 114. Upon collision, the microbe particles 150 specifically bind to the antibodies 151 attached to the surface of the trapping plate 114, and are trapped on the surface of the trapping plate 114.

(2) Labeling Step

The control section 125 determines whether a preset trap time ta (min) has elapsed (step S330). The labeling step starts after an elapse of trap time ta (min) (step S340).

In the labeling step, the valve 1312 provided for the pipe branching out of the connecting tube 1281 and connecting to the atomizer 123 is opened. Another valve that is opened in this step is the valve 1313 provided for the pipe 133 connecting the pump 122 to the vent hole 1011 that is in communication with the upstream side of the waste liquid container 103, and to the vent hole 1012 that is in communication with the downstream side of the washing liquid container 102.

Operating the pump 122 thus draws the mist 153 containing the fluorescent dye 154 and generated by the atomizer 123 into the cartridge 10 through the inlet 100, and the mist 153 is trapped inside the cartridge 10, as shown in FIG. 8B. Here, the mist 153 passes through the micropores 115 of the porous plate 112, and collides with the trapping plate 114. Upon collision, the mist 153 collides with the microbe particles 150 trapped on the surface of the trapping plate 114, causing the fluorescent dye 154 in the mist 153 to specifically bind to the microbe particles 150.

(3) Washing Step

The control section 125 determines whether a preset labeling time tb (min) has elapsed (step S350). The washing step starts after an elapse of labeling time tb (min) (step S360).

In the washing step, the valve 1314 provided for the pipe 134 connected to the vent hole 1013 that is in communication with the upper end portion of the washing liquid container 102, and the valve 1315 provided for the pipe 132 connected to the vent hole 1014 that is in communication with the upper end portion of the waste liquid container 103 are opened.

Operating the pump 122 thus draws the washing liquid 1021 inside the washing liquid container 102 into the trapping detector 104 through the channel 1051 connecting the washing liquid container 102 and the trapping detector 104, as shown in FIG. 8C. The washing liquid 1021 then flows into the waste liquid container 103 through the channel 1052 connecting the trapping detector 104 and the waste liquid container 103. Here, the fluorescent dye 154 that has non-specifically adsorbed to the trapping plate 114 is removed with a stream 155 (see FIG. 8C). The fluorescent dye 154 that has non-specifically adsorbed to the trapping plate 114 becomes an obstacle of the microbe detection, and is removed as much as possible to improve detection accuracy.

(4) Detection Step

The control section 125 determines whether a preset washing time tc (min) has elapsed (step S370). The detection step starts after an elapse of washing time tc (min) (step S380). In the detection step, the optical detector 124 shines excitation light on the trapping plate 114 of the cartridge 10, and detects the generated fluorescence from the fluorescent dye 154 specifically binding to the microbe particles 150, thereby detecting the microbe particles 150.

FIG. 9 schematically illustrates an example of the optical system of the optical detector 124. The optical detector 124 includes a light source 143, an excitation light condensing lens 1412, a dichroic mirror 1421, an objective lens 1411, a band-pass filter 1422, a mirror 1423, a fluorescence condensing lens 1413, and a photodetector 144.

The light source 143 generates excitation light. The excitation light condensing lens 1412 condenses the excitation light from the light source 143. The dichroic mirror 1421 reflects the wavelengths of the excitation light, and passes the wavelengths of the fluorescence from the fluorescent dye binding to the microbe particles 150. The excitation light falls on the trapping plate 114 through the objective lens 1411, and the fluorescence from the fluorescent dye binding to the microbe particles 150 is condensed by the objective lens 1411. The band-pass filter 1422 passes only the wavelengths of the fluorescence light. The mirror 1423 is used to change the light path of the fluorescence. The fluorescence condensing lens 1413 condenses the fluorescence onto the photodetector 144. The photodetector 144 transduces the light energy of the fluorescence into electrical energy.

The light source 143 uses any of a laser, an LED, a mercury lamp, and a halogen lamp. The photodetector 144 uses a photomultiplier or a semiconductor light sensor. When the shape of the microbe particles 150 trapped on the trapping plate 114 needs to be known, an image capturing device such as a CCD is used instead of the photodetector 144.

Light of 300 nm to 800 nm wavelengths is used as the excitation light. Autofluorescence from the trapping plate 114 and the porous plate 112 can be reduced by making the wavelength of the excitation light longer. It is therefore preferable to use light having a wavelength of 600 nm or more. The fluorescence wavelength is longer than the excitation light wavelength, though it depends on the type of the fluorescent dye.

In the detection step, the fluorescence from the microbe particles 150 trapped on the trapping plate 114 is obtained as a voltage value in the photodetector 144 (step S390). The control section 125 compares the output value of the photodetector 144 with the predetermined value Y (mV) (step S400). The value Y is a measured voltage value obtained by the photodetector 144 from the fluorescence generated from the trapping plate 114 in the absence of the trapped microbe particles. The value Y is measured at a certain time point immediately before the transition from the trapping step to the labeling step. The output to the display section 126 is "positive" when the detected value by the photodetector 144 is greater than the predetermined value Y (mV) (step S410), and is "Negative" when the detected value by the photodetector 144 is equal to or less than the predetermined value Y (mV).

Example 2

In the labeling step of Example 1, the binding of the fluorescent dye with the microbe particles occurs as a result of the fluorescent dye-containing mist colliding with the microbe particles. However, the binding of the fluorescent dye with the microbe particles also may be achieved by flowing a fluorescent dye-containing liquid against the trapping plate surface trapping the microbe particles. In this Example, the microbe particles are labeled by flowing a fluorescent dye-containing liquid against the trapping plate surface.

FIG. 10 shows another example of the cartridge according to the invention. A cartridge 20 has a mechanism to maintain liquid inside the cartridge 20, and to perform the steps necessary for trapping and detecting the microbes present in breath or air. FIG. 10 is a perspective view as viewed from the back side of the cartridge 20, and corresponds to FIG. 2B.

In this Example, the cartridge 20 includes a dye solution container 206 as a reagent solution container, and a channel 2051 connecting the dye solution container 206 to the washing liquid container 102 and branching out from the channel 1051 connecting the washing liquid container 102 to the trapping detector 104, in addition to the configuration of the cartridge 10 described in Example 1. The dye solution container 206 is disposed above the trapping detector 104, and stores a fluorescent dye solution 2061 that specifically binds to microbes. The channel 2051 is in communication with the dye solution container 206 and the trapping detector 204, and is provided for the passage of the dye solution 2061.

Figure 11:
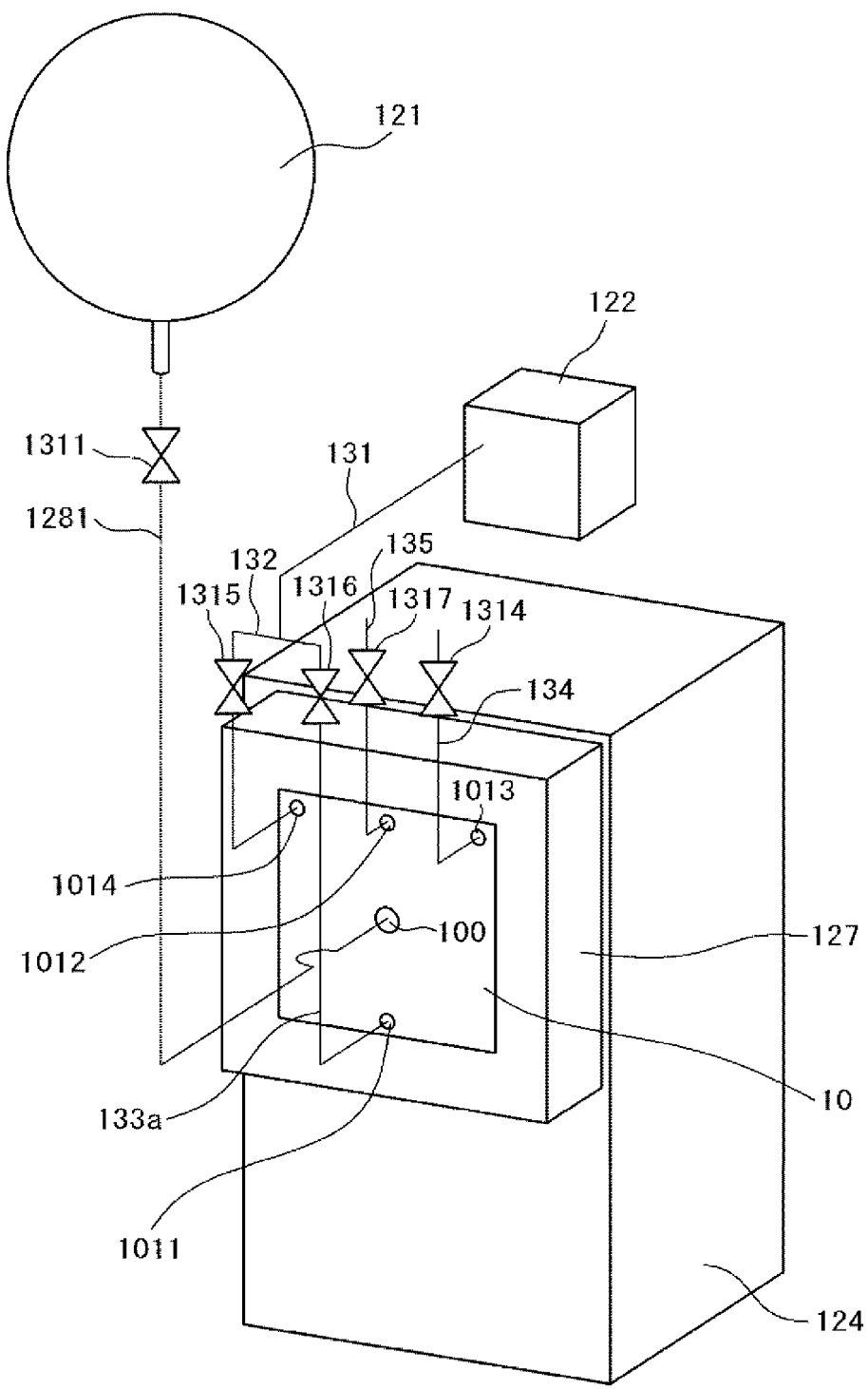
FIG. 11 is a piping system diagram of a breath microbe detection device with the cartridge shown in FIG. 10.

FIG. 11 is a piping system diagram of the breath microbe detection device 1 according to this Example. The pipe 133a connected to the vent hole 1011 that is in communication with the upstream side of the waste liquid container 103 is not in communication with the vent hole 1046 that is in communication with the downstream side of the washing liquid container 102. Instead, a pipe 135 is provided that is connected to the vent hole 1012 that is in communication with the upper end portion of the dye solution container 1206. A valve 1317 is interposed in the pipe 135, and the end of the pipe 135 is open to the atmosphere. The pipe 1281 connecting the breath bag 121 to the inlet 100 does not have a pipe that branches into the atomizer, but is directly connected to the inlet 100.

Figure 12A:
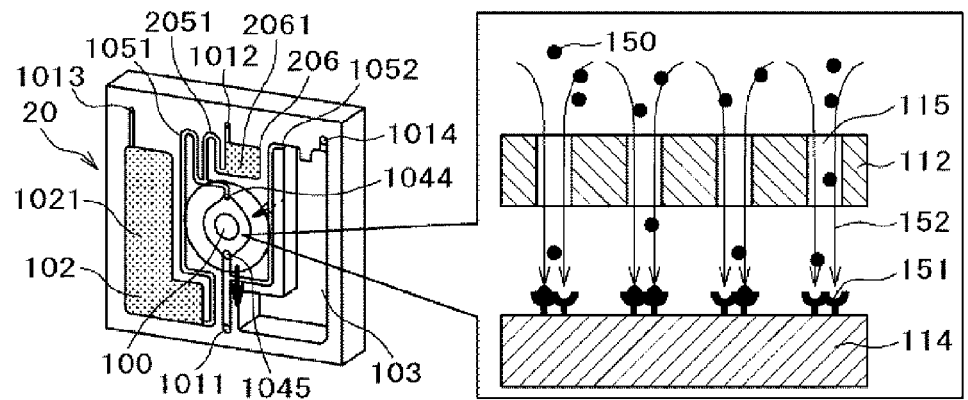
FIG. 12A is a diagram representing the operation of the cartridge shown in FIG. 10, explaining the microbe trapping step.
Figure 12B:
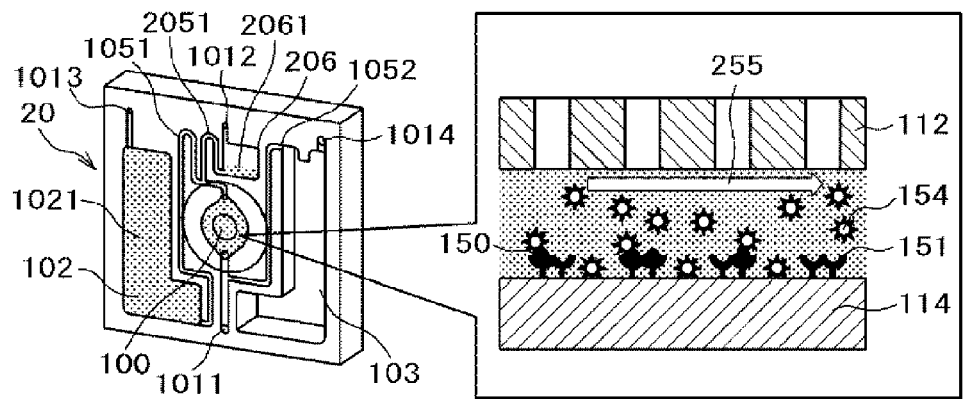
FIG. 12B is a diagram representing the operation of the cartridge shown in FIG. 10, explaining the microbe labeling step.
Figure 12C:
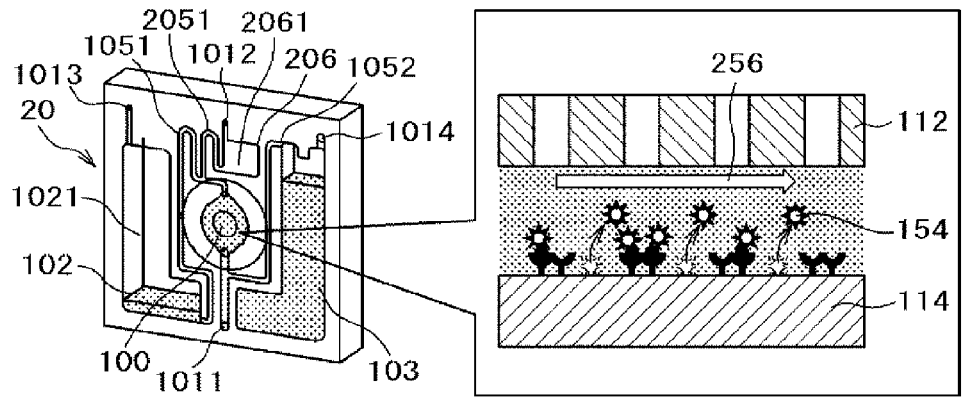
FIG. 12C is a diagram representing the operation of the cartridge shown in FIG. 10, explaining the microbe washing step.

In this Example, detection of breath microbe particles proceeds as shown in the flowchart of in FIG. 7, as in Example 1. FIGS. 12A to 12C are diagrams representing the trapping, labeling, and washing steps of the breath microbe particles detection procedure. The figures show the flow state inside the cartridge 20, and the flow state of the microbe particles 150 and the fluorescent dye 154 against the trapping plate 114.

Table 2 presents the open/close states of the valves 1311 to 1317, and the operating states of the pump 122 and the optical detector 124 in the trapping, labeling, washing, and detection steps of the breath microbe detection procedure represented in FIG. 7.

TABLE 2

| Step | Valve | | | | | Pump | Detector |
| | 1311 | 1316 | 1317 | 1314 | 1315 | 122 | 124 |
|---|---|---|---|---|---|---|---|
| Trapping | Open | Open | Closed | Closed | Closed | On | Off |
| Labeling | Closed | Closed | Open | Closed | Open | On | Off |
| Washing | Closed | Closed | Closed | Open | Open | On | Off |
| Detection | Open | Open | Open | Open | Open | Off | On |

(1) Trapping Step

The valve 1311 provided for the pipe 1281 connecting the breath bag 121 to the inlet 100 of the cartridge 20 is opened. The valve 1312 provided for the pipe 133a connecting the pump 122 and the vent hole 1011 that is in communication with the upstream side of the waste liquid container 10 is also opened. Operating the pump 121 draws the breath out of the breath bag 121 into the inlet 100 and the vent hole 1011 of the cartridge 20, as shown in FIG. 12A.

The valve 1317 provided for the pipe 135 connected to the vent hole 1012 that is in communication with the upper end portion of the dye solution container 206 is closed. The valve 1314 provided for the pipe 134 connected to the vent hole 1013 that is in communication with the upper end of the washing liquid container 102 is also closed. The valve 1315 provided for the pipe 132 connected to the vent hole 1014 that is in communication with the upper end of the waste liquid container 103 is also closed. With these valves closed, the dye solution 2061 contained in the dye solution container 206, and the washing liquid 1021 contained in the washing liquid container 102 of the cartridge 20 remain in their respective containers 206 and 102.

Here, the microbe particles 150 contained in the breath pass through the micropores 115 of the porous plate 112, and collide with the trapping plate 114. Upon collision, the microbe particles 150 specifically bind to the antibodies 151 binding to the surface of the trapping plate 114, and are trapped on the surface of the trapping plate 114.

(2) Labeling Step

A transition to the labeling step occurs after an elapsed preset trap time to (min). In the labeling step, the valve 1317 provided for the pipe 135 connected to the vent hole 1012 that is in communication with the upper end of the dye solution container 206, and the valve 1315 provided for the pipe 132 connected to the vent hole 1014 that is in communication with the upper end of the waste liquid container 103 are opened.

Operating the pump 222 draws the dye solution 2061 out of the dye solution container 206 of the cartridge 20 into the trapping detector 104 through the channel 2051 connecting the dye solution container 206 to the trapping detector 104, as shown in FIG. 12B. The dye solution 2061 then flows into the waste liquid container 103 through the channel 1052 connecting the trapping detector 104 to the waste liquid container 103. Here, the liquid containing the fluorescent dye 154 flows over the trapping plate 114 in the form of a stream 255. The fluorescent dye 154 in the stream specifically binds to the microbe particles 150 trapped on the surface of the trapping plate 114.

(3) Washing Step

A transition to the washing step occurs after an elapsed preset labeling time tb (min). In the washing step, the valve 1314 provided for the pipe 134 connected to the vent hole 1013 that is in communication with the upper end of the washing liquid container 102, and the valve 1315 provided for the pipe 132 connected to the vent hole 1014 that is in communication with the upper portion of the waste liquid container 103 are both opened.

Operating the pump 222 draws the washing liquid 1021 out of the washing liquid container 102 into the trapping detector 104 through the channel 1051 connecting the washing liquid container 102 to the trapping detector 104, as shown in FIG. 12C. The washing liquid 1021 then flows into the waste liquid container 103 through the channel 1052 connecting the trapping detector 104 to the waste liquid container 103. Here, the fluorescent dye 154 that has non-specifically adsorbed to the trapping plate 114 is removed with a stream 256.

(4) Detection Step

A transition to the detection step occurs after an elapsed preset washing time tc (min). In the detection step, the optical detector 124 shines excitation light on the trapping plate 114 installed in the cartridge 20. Under the excitation light, the fluorescent dye 154 binding to the microbe particles 150 generates fluorescence. The optical detector 124 detects the generated fluorescence to detect the microbe particles 150.

As described above in the Examples of the invention, contamination in the main body of the breath microbe detection device can be reduced as much as possible by the provision of the impactor porous plate and trapping plate in the disposable cartridge. This reduces detection errors even after many uses. Further, by the provision of the transparent detection surface arranged opposite the trapping surface used as the cartridge impactor, it is possible to perform optical detection from the back side, and to provide a compact breath microbe detection device. Further, because a tester only needs to install the breath bag, the procedure does not qualify as medical practice, and can automatically detect microbes in a short time period.

Instead of using the porous plate as in the foregoing Examples, detection may be performed with a single micropore when the target substance of detection is relatively large. In this way, the detection target substance can be more accurately identified.

REFERENCE SIGNS LIST

1: Breath microbe detection device (airborne-substance detection device)
10, 20: Cartridge
100: Inlet
102: Washing liquid container
103: Waste liquid container
104: Trapping detector
106: Reagent container
110: Main body
111: Adhesive layer
112: Porous plate (inflow plate)
113: Spacer
114: Trapping plate
115: Micropore
116: Vent hole
120: Casing
121: Breath bag
122: Pump
123: Atomizer
124: Optical detector
125: Control section
126: Display section
127: Cartridge holder
128: Lid
131: Intake pipe
132 to 135: Pipe
143: Light source
144: Photodetector
150: Microbe particles
151: Antibody
153: Mist
154: Fluorescent dye
155: Stream
206: Dye solution container (reagent container)
255, 256: Stream
1011 to 1014: Vent hole
1021: Washing liquid
1041 to 1044: Communication hole
1045, 1046: Junction
1051, 1052: Communication channel
1061: Reagent
1101: Groove
1131: Opening
1222: Arrow
1241: Excitation light
1242: Fluorescence
1281: Connecting tube
1282: Attachment opening
1283: Window
1311 to 1317: Valve
1411: Objective lens
1412: Excitation light condensing lens
1413: Fluorescence condensing lens
1421: Dichroic mirror
1422: Band-pass filter
1423: Mirror
2051, 2052: Connection channel
2061: Dye solution
ta to tc: Time
Lx to Lz: Dimensions

The invention claimed is:

1. A cartridge for airborne-substance detection devices, the cartridge comprising:
an inflow plate having formed therein a micropore that allows inflow of a microparticle-containing gas;
a trapping plate disposed opposite the micropore and having the ability to capture the microparticles on a surface facing the micropore; and
a main body in which the inflow plate and the trapping plate are installed, and in which a channel is formed that channels the microparticle-containing gas to the micropore,
wherein the trapping plate is disposed on the outermost side of the cartridge with the trapping surface facing inward, and is configured from a light transmissive member.

2. The cartridge for airborne-substance detection devices according to claim 1,
wherein a gap is formed between the inflow plate and the trapping plate disposed opposite each other, and
wherein the main body includes:
at least one storage container for storing a liquid;
a waste liquid container for retaining the liquid flowed out of the storage container and passed through the gap between the inflow plate and the trapping plate; and
a channel connecting the gap and the waste liquid container to each other, and a channel connecting the gap and the storage container to each other.

3. The cartridge for airborne-substance detection devices according to claim 2, wherein an adhesive substance or a substance capable of specifically binding to the microparticles is bound or adsorbed to the microparticle-capturing surface of the trapping plate.

4. The cartridge for airborne-substance detection devices according to claim 2, wherein the microparticles which can be captured are at least one selected from viruses, bacteria, yeasts, protozoa, fungi, spores, pollen, fragmented animal skin, feces or dead bodies of mites, house dust, gas emission particles, and ore particles.

5. The cartridge for airborne-substance detection devices according to claim 2, wherein the inflow plate has a plurality of micropores, and is light transmissive.

* * * * *